United States Patent
Cape et al.

(10) Patent No.: US 10,471,152 B2
(45) Date of Patent: Nov. 12, 2019

(54) COLLOIDAL DISPERSION COMPRISING HPMCAS

(71) Applicant: Capsugel Belgium NV, Bornem (BE)

(72) Inventors: Jonathan Leonard Cape, Bend, OR (US); Warren Kenyon Miller, Bend, OR (US); Dwayne Thomas Friesen, Bend, OR (US); Hassan Benameur, Eaubonne (FR); Maryline Clauzel, Wickerschwihr (FR); David Thomas Vodak, Bend, OR (US)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/507,226

(22) PCT Filed: Aug. 19, 2015

(86) PCT No.: PCT/EP2015/068983
§ 371 (c)(1),
(2) Date: Feb. 27, 2017

(87) PCT Pub. No.: WO2016/030234
PCT Pub. Date: Mar. 3, 2016

(65) Prior Publication Data
US 2017/0281780 A1    Oct. 5, 2017

Related U.S. Application Data

(60) Provisional application No. 62/044,003, filed on Aug. 29, 2014.

(51) Int. Cl.
| | |
|---|---|
| A61K 47/38 | (2006.01) |
| A61K 9/10 | (2006.01) |
| A61K 9/48 | (2006.01) |
| A61K 47/14 | (2017.01) |
| A61K 9/50 | (2006.01) |
| B29L 31/00 | (2006.01) |

(52) U.S. Cl.
CPC ............... *A61K 47/38* (2013.01); *A61K 9/10* (2013.01); *A61K 9/4816* (2013.01); *A61K 9/4833* (2013.01); *A61K 9/5042* (2013.01); *A61K 47/14* (2013.01); *B29L 2031/7174* (2013.01)

(58) Field of Classification Search
None
See application file for complete search history.

(56) References Cited

U.S. PATENT DOCUMENTS

| | | | |
|---|---|---|---|
| 2,718,667 A | 9/1955 | Maim et al. | |
| 3,493,407 A | 2/1970 | Greminger et al. | |
| 3,617,588 A | 11/1971 | Langman | |
| 4,001,211 A | 1/1977 | Sarkar | |
| 4,111,202 A | 9/1978 | Theeuwes | |
| 4,138,013 A | 2/1979 | Okajima | |
| 5,264,223 A | 11/1993 | Yamamoto et al. | |
| 5,508,276 A * | 4/1996 | Anderson ............ | A61K 31/381 514/183 |
| 5,756,123 A | 5/1998 | Yamamoto et al. | |
| 5,851,579 A | 12/1998 | Wu et al. | |
| 5,910,319 A | 6/1999 | Anderson et al. | |
| 7,138,143 B1 | 11/2006 | Mukai et al. | |
| 9,452,141 B1 | 9/2016 | Chang et al. | |
| 2012/0161364 A1 | 6/2012 | Son et al. | |
| 2013/0295188 A1 | 3/2013 | Cade et al. | |
| 2017/0157058 A1 | 6/2017 | Chang et al. | |

FOREIGN PATENT DOCUMENTS

| | | | |
|---|---|---|---|
| EP | 0 401 832 | 12/1990 | |
| EP | 0 648 487 | 4/1995 | |
| EP | 2 476 439 | 7/2012 | |
| EP | 2476439 A1 * | 7/2012 | ............ A61K 47/38 |
| EP | 3 178 473 A1 | 6/2017 | |
| GB | 1310697 | 3/1973 | |
| JP | S58-138458 A | 8/1983 | |
| JP | 2006-016372 A | 1/2006 | |
| TW | 200520790 A | 7/2005 | |
| TW | 1587880 B | 6/2017 | |
| WO | WO 2004/030658 | 4/2004 | |
| WO | WO 2008/050209 | 5/2008 | |
| WO | WO 2008/119943 | 10/2008 | |
| WO | WO 2011/030952 | 3/2011 | |
| WO | WO 2011/155686 | 12/2011 | |
| WO | WO-2013/164121 | 7/2013 | |

OTHER PUBLICATIONS

Felton, L.A. et al., "Enteric Film Coating of Soft Gelatin Capsules," *Drug Development and Delivery*, 3(6), (Sep. 2003, posted Mar. 28, 2008).

International Search Report and Written Opinion, dated Aug. 12, 2015, issued in corresponding International Application No. PCT/EP2015/068983, 9 pages.

ShinEtsu (AQOAT, Hypromellose Acetate Succinate, [Retrieved from Internet <URL: http://www.metolose.jp/e/pharmaceutical/aqoat.shtml>], Copyright 2001-2013, [Retrieved Jan. 24, 2017], 1 page).

Thoma et al., "Enteric coated hard gelatin capsules," *Capsugel Technical Bulletin* 1986, 17 pages.

* cited by examiner

*Primary Examiner* — Monica A Shin (74) *Attorney, Agent, or Firm* — Klarquist Sparkman, LLP (57) ABSTRACT

The present disclosure relates to compositions of an aqueous colloidal dispersion of hydroxypropyl methyl cellulose acetate succinate (HPMCAS), and methods for making such colloidal dispersions.

13 Claims, 3 Drawing Sheets

COLLOIDAL DISPERSION COMPRISING HPMCAS

CROSS REFERENCE TO RELATED APPLICATIONS

This is the U.S. National Stage of International Application No. PCT/EP2015/068983, filed Aug. 19, 2015, which was published in English under PCT Article 21(2), which in turn claims the benefit of U.S. Provisional Application No. 62/044,003, filed Aug. 29, 2014. The provisional application is incorporated herein in its entirety.

The present disclosure relates to compositions of an aqueous colloidal dispersion of hydroxypropyl methyl cellulose acetate succinate (HPMCAS), and methods for making such colloidal dispersions.

BACKGROUND

WO 2013/164121 discloses aqueous compositions for use in the manufacture of capsule shells having bulk enteric properties. The HPMCAS is partially neutralized in such aqueous dispersions to render the compositions suitable for the implementation of the capsule shell manufacturing process. The aqueous dispersions further contain a polymeric gelling agent that undergoes thermal gelation in response to a change in temperature.

SUMMARY

In one aspect, an aqueous-based composition comprises a colloidal dispersion comprising hydroxypropyl methylcellulose acetate succinate (HPMCAS) polymer. The colloidal dispersion further comprises a dispersant, a plasticizer, and a non-polymeric, ionizable surface modifier. More specifically, the non-polymeric, ionizable surface modifier is selected from the group consisting of organic acids and compounds of multivalent cations. The aqueous-based compositions have appropriate solid content, viscosity at room temperature, setting properties, and rheological behavior for use in the manufacture of capsule shells. The aqueous-based compositions are capable of thermogelling in the absence of a conventional thermogelling polymer.

In another aspect, the present disclosure relates to films and capsule shells obtained from the aqueous-based compositions. The films and/or capsule shells display bulk enteric properties and exhibit optimal chemical and mechanical properties, e.g., disintegration profile, dissolution profile, film thickness, and combinations thereof.

In another aspect, the present disclosure provides processes for making the disclosed aqueous-based compositions. The process includes dissolving HPMCAS and a plasticizer in an organic solvent to form an organic phase; combining water, a dispersant, and a base to form an aqueous phase; combining the organic phase and the aqueous phase to form a mixture; homogenizing the mixture to form an emulsion; removing substantially all of the organic solvent from the mixture; adjusting the water concentration of the mixture to obtain an aqueous dispersion of HPMCAS, and adding a non-polymeric, ionizable surface modifier to the aqueous dispersion. More specifically, the non-polymeric, ionizable surface modifier is selected from the group consisting of organic acids and compounds of multivalent cations.

In another aspect, the present disclosure relates to processes for making films and capsule shells from the disclosed aqueous-based compositions. The colloidal dispersions include individual (pseudo)latex particles which, in the presence of sufficient percent solids, aggregate into a continuous packed structure. The aggregated colloidal dispersions are capable of forming films, and are suitable for use in manufacture of capsules, e.g., using conventional dip molding techniques.

DESCRIPTION

Definitions:

As used in the present disclosure, the following words, phrases, and symbols are generally intended to have the meanings as set forth below, except to the extent that the context in which they are used indicates otherwise.

As used herein, "optional" or "optionally" means that the subsequently described material, event or circumstance may or may not be present or occur, and that the description includes instances where the material, event or circumstance is present or occurs and instances in which it does not.

As used herein, "w/w %" and "wt %" means by weight as a percentage of the total weight or relative to another component in the composition.

As used herein, "wt % solids" means the weight of the solid component(s) of the composition as a percentage of the total composition.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

The term "room temperature" refers to temperatures ranging from 15° C. to 25° C. and preferably 20° C. to 25° C.

The term "solution" refers to a single phase system.

The term "dispersion" refers to a two phase system where one phase consists of finely divided solid particles.

The term "colloidal dispersion" refers to a dispersion comprising particles having a diameter range of from 0.001 to 100 µm.

The term "gel" refers to a physical state of a substance in which it mechanically behaves like an elastically deformable solid over a range of timescales and stresses. More specifically, a gel refers to a rheological state of a liquid or semisolid in which it exhibits a dominant elastic response as rheologically characterized by dynamic mechanical properties such as the storage and loss moduli. In particular, the gel state of a substance is rheologically defined over a range of timescales and stress or strain values in which the substance's storage modulus is greater than its loss modulus.

The term "gelation" refers to the process of becoming gel, e.g., transition from a viscous liquid state to a gel state during a change in temperature or concentration.

The term "cold gelation" refers to a gelation that occurs due to a decrease in the temperature of a particular material or substance below its characteristic gelation temperature.

The terms "thermogelation" and "thermal gelation" are synonymous and refer to gelation occurring due to an increase in the temperature of a particular material or substance above its characteristic gelation temperature.

Unless otherwise indicated, "capsule" means a container suitable for enclosing solids or liquids, and includes empty capsule shells and components thereof such as caps and bodies that may be assembled together to form the capsule.

Unless otherwise indicated, "dosage form" refers to a solid composition comprising an active ingredient.

The term "active ingredient" means any compound or component that is pharmaceutically or physiologically active, or provides a beneficial effect to a patient. Examples of active ingredients include acetaminophen, ibuprofen, and caffeine.

Unless otherwise indicated, "bulk enteric properties" means that the capsules described herein are soluble in, or disintegrated by alkaline intestinal secretions, but are substantially insoluble or resistant to disintegration in acid secretions of the stomach. These enteric properties are intrinsic to the capsule shells and capsules as manufactured, i.e., no further coating or other post-manufacturing treatment is necessary to impart these enteric properties. Disintegration and dissolution properties can be tested according to monographs <701>, USP34-NF29, page 276; <711>, USP34-NF29, page 278; and <2040>, USP34-NF29, page 871.

As used herein, the term "substantially free from" means the material is not present in the composition (e.g., colloidal dispersion or capsule as the case may be) in an amount of greater than 0.1 wt %.

Materials and Composition

In one embodiment, an aqueous colloidal dispersion comprises HPMCAS, a plasticizer, a dispersant, and a non-polymeric, ionizable surface modifier. The colloidal dispersion is useful for the manufacture of capsule shells.

HPMCAS

Unless otherwise indicated, HPMCAS means the polymer hydroxypropyl methylcellulose acetate succinate. HPMCAS is commonly known in the field of polymers with the following alternative nomenclature: CAS registry number 71138-97-1; chemical common synonyms, such as: Hypromellose Acetate Succinate; HPMC-AS; Cellulose, 2-hydroxypropylmethylether, acetate, hydrogen butanedioate.

Examples of commercially available HPMCAS are Shin-Etsu AQOAT®, Dow AFFINISOL™ HPMCAS, and Ashland AQUASOLVE AS™. The polymer is available from Shin-Etsu in micronized grade (LF, MF, HF) with mean particle size of 5 microns (μm) or granular grade (LG, MG, HG) with mean particle size of 1 mm. HPMCAS contains not less than 4% and not more than 18% of succinoyl groups, and not less than 5% and not more than 14% acetyl groups. The L, M and H grades available from Shin-Etsu have different degrees of succinoyl and acetyl substitution so as to vary the pH at which the polymer begins to dissolve. Any such grade may be suitable for use in the colloidal dispersion.

The HPMCAS is partially neutralized in the colloidal dispersion composition. "Partially neutralized" means that only a portion of the succinic acid groups present in the HPMCAS polymer is neutralized or converted from the protonated to anionic form by addition of an alkaline material (such as a base), and the rest of the succinic acid groups remain in the acid or protonated form. The percentage of neutralization of HPMCAS is defined as the ratio of the amount of acidic groups on the polymer that are in either in the deprotonated or anionic state relative to the total amount of acidic, or succinic acid groups on the polymer. In one embodiment, the percentage neutralization of the HPMCAS is from 0 to 50%.

The amount of HPMCAS present in the colloidal dispersion may range from 5.0 to 45.0 wt % of the colloidal dispersion composition. More preferably, the amount of the amount of HPMCAS present in the colloidal dispersion may range from 10 to 40 wt %, or more preferably from 15 to 35 wt % of the colloidal dispersion composition.

The amount of HPMCAS present in the colloidal dispersion relative to the other solids present in the colloidal dispersion may range from 60.0 to 99.0 wt % dry matter.

Dispersant

The colloidal dispersion composition also comprises a dispersant. The dispersant may be a non-ionic or anionic surfactant. Examples of dispersants include anionic alkyl sulfates, and non-ionic dispersants such as polysorbates and polyethylene oxide/polypropylene oxide block copolymers (e.g. poloxamers), and polyvinylalcohol. Examples of alkyl sulfates include sodium octyl sulfate, sodium decyl sulfate, and sodium dodecyl sulfate. Examples of non-ionic surfactants include polysorbate 20, polysorbate 65, polysorbate 80, poloxamer 188, poloxamer 124, and poloxamer 407. A preferred anionic dispersant is sodium dodecyl sulfate, also referred to as sodium lauryl sulfate. A preferred non-ionic dispersant is polysorbate-80.

The dispersant is present in a sufficient amount to stabilize the organic emulsion of the polymer in water during processing of the colloidal dispersion.

The amount of anionic dispersant may range from 0.1 to 5.0 wt % relative to the amount of HPMCAS in the colloidal dispersion composition. More preferably the anionic dispersant may range from 1.0 to 3.5 wt % of the HPMCAS in the colloidal dispersion composition.

The amount of non-ionic dispersant may range from 0.1 to 40.0 wt % relative to the amount of HPMCAS in the colloidal dispersion composition. More preferably the non-ionic dispersant may range from 1.0 to 15.0 wt % of the HPMCAS in the colloidal dispersion composition.

Plasticizer

The colloidal dispersion composition also comprises a plasticizer. The plasticizer preferably is miscible with HPMCAS at the amounts used in the colloidal dispersion. In addition, the plasticizer preferably partitions into the HPMCAS relative to aqueous solution. Examples of plasticizers include acetylated-alkyl citrates, alkyl phthalates, mono and di-glycerol esters, and benzoate-esters.

Examples of tri-alkyl citrate esters include triethyl citrate (TEC), acetyl triethyl citrate (ATEC), acetyl tributyl citrate (ATBC), tributyl citrate (TBC), trioctyl citrate (TOC), acetyl trioctyl citrate (ATOC), trihexyl citrate (THC), acetyl trihexyl citrate (ATHC), butyryl trihexyl citrate (BTHC), trihexyl o-butyryl citrate (THBC), and trimethyl citrate (TMC).

Examples of benzoates include benzyl benzoate.

Other suitable plasticizers include: phthalate esters (e.g. dimethyl-, diethyl-, dibutyl-, diisopropyl- and dioctyl-phthalate); phosphoric esters (e.g. triethyl-, tricresyl, triphenyl-phosphate); alkyl lactate; glycerol and glycerol esters (e.g. glycerol triacetate also known as triacetine); sucrose esters; oils and fatty acid esters; butyl stearate; dibutyl sebacate; dibutyl tartrate; diisobutyl adipate, tributyrin; propylene glycol; polyethyleneglycol (PEG); polyoxyethylene (PEO) and polysorbates (PS); and mixtures thereof.

The plasticizer is present in a sufficient amount to achieve suitable film forming properties in the colloidal dispersion during the drying process as well as suitable mechanical properties in the final dried film. The total amount of plasticizer may range from about 0 to 40.0 wt % relative to the amount of HPMCAS present in the colloidal dispersion composition. More preferably, the total amount of plasticizer may range from about 5 to 40 wt % or from about 15 to 30 wt % relative to the amount of HPMCAS present in the colloidal dispersion composition. More than one plasticizer may be present in the colloidal dispersion.

Non-Polymeric, Ionizable Surface Modifier

The colloidal dispersion composition also comprises a non-polymeric, ionizable surface modifier. The function of the non-polymeric, ionizable surface modifier is to interact with the acidic groups on the surface of the colloidal dispersion particles. In general, the non-polymeric, ionizable surface modifier is ionizable and can interact with the HPMCAS and other compounds of the composition by protonation, deprotonation and ion-pairing interactions. Colloidal dispersions prepared in this manner aggregate into films when heated.

By non-polymeric it is meant that the non-polymeric, ionizable surface modifier is not a polymer. The molecular weight of the non-polymeric, ionizable surface modifier may be less than 1000 daltons. In one embodiment, the molecular weight of the non-polymeric, ionizable surface modifier is less than 200 daltons, and may be less than 100 daltons.

By "ionizable" is meant that the non-polymeric, ionizable surface modifier has the capability of existing in either the ionized or non-ionized states in the colloidal dispersion. In one embodiment, non-polymeric, ionizable surface modifier is in neutral form when protonated and is in anionic form when deprotonated. In another embodiment, the non-polymeric, ionizable surface modifier is in neutral form when associated with a counter ion of opposite charge and ionized when dissociated from the paired ion.

Examples of the non-polymeric ionizable surface modifiers include organic acids and compounds of multivalent cations.

Examples of organic acids suitable for use as a non-polymeric, ionizable surface modifier include saturated- or unsaturated-, linear- or branched-aliphatic carboxylic acids, dicarboxylic acids, hydroxy carboxylic acids, and benzoic acids. Examples of aliphatic carboxy acids include formic, acetic, propionic, butyric, pentanoic, and hexanoic acids. Examples of dicarboxylic acids include oxalic, malonic, and succinic acids. Examples of hydroxy carboxylic acids include glycolic, lactic, malic, tartaric, citric and mandelic acids. Other examples of organic acids include alkyl and aryl sulfonic and sulfuric acids and polyacids, alkyl and aryl phosphonic and phosphoric acids and polyacids, and acid salts of primary, secondary and tertiary amines.

Examples of multivalent cations suitable for use as the non-polymeric, ionizable surface modifiers include alkaline earth metals and first and second row transition metals. Preferred multivalent cations are calcium and magnesium.

Such multivalent cations generally exist as compounds that are paired with one or more counter ions. Examples of suitable counter ions for use with multivalent cations include: chloride, sulfate, hydroxide, acetate, perchlorate, nitrate, iodide, bromide, and carbonate. Examples of compounds suitable for use as non-polymeric, ionizable surface modifiers include calcium chloride, calcium hydroxide, calcium acetate, magnesium chloride, magnesium hydroxide, and magnesium acetate. When the surface modifier is a multivalent cation hydroxide, e.g., calcium hydroxide, the surface modifier also may function as an alkaline material wherein the hydroxide ions partially neutralize a portion of the succinic acid groups on the HPMCAS polymer, and the calcium cations then bind to the carboxyl groups to facilitate aggregation.

In an independent embodiment, the multivalent cation compound is a salt. As used herein, the term "salt" refers to the product formed by reaction of a base and a mineral acid (e.g., HCl, HBr, HI, $HNO_3$, $HClO_4$, $H_2SO_4$) or an aliphatic carboxylic acid (e.g., acetic acid, carbonic acid). Salts contain both cationic and anionic components, combined together to make a neutral compound. In particular, the salt is not formed by reaction of a base and an alcohol, i.e., the salt is not an alkoxide. Examples of suitable anions are chloride, sulfate, acetate, perchlorate, nitrate, iodide, bromide, and carbonate. In some embodiments, the cationic components of salts are calcium or magnesium. Preferred salts for use as the non-polymeric, ionizable surface modifier are calcium chloride, calcium acetate, magnesium chloride, and magnesium acetate.

Compounds of multivalent cations may be used in solid or liquid mixtures with other compounds of multivalent cations, dissolved in water, or mixed with other non-functional or functional materials.

The non-polymeric, ionizable surface modifier is present in a sufficient amount such that the ratio of moles of non-polymeric ionizable surface modifier to moles of succinate groups on the HPMCAS ranges from about 0.01 to 10. Preferably, the amount of non-polymeric, ionizable surface modifier may range from 0.02% to 10.0% of the amount of HPMCAS in the colloidal dispersion composition. More preferably, the amount of non-polymeric, ionizable surface modifier may range from 0.05% to 7.0% of the amount of HPMCAS in the colloidal dispersion composition.

Optional Materials

The colloidal dispersion composition may contain other optional materials so long as such materials do not interfere with the thermogelling property of the colloidal dispersion. In some cases, the optional materials may promote the thermogelling property of the colloidal dispersion.

In another embodiment, the aqueous compositions may comprise an anti-foaming agent. The anti-foaming agent may be added during preparation of the colloidal dispersion, such as after evaporation of the organic solvent from the emulsion. Examples of anti-foaming agents include polydimethylsiloxanes, for example sold under the trade names Silfar SE-4, AntiFoam A, AntiFoam $C_6$, AntiFoam Y30 and Simethicone. The amount of the anti-foaming agent may range from 0.01 to 0.1 wt % of the colloidal dispersion.

In another embodiment, the aqueous compositions may comprise an optional film-forming polymer, such as those conventionally used as base film-forming polymers for hard capsule shells. Examples of film-forming polymers include cellulose derivatives such as hydroxypropyl methyl cellulose (HPMC), and methylcellulose, gelatin, pullulan, PVA, starch and starch derivatives, such as hydroxypropyl starch as disclosed in WO 2013/164121.

The amount of the film-forming polymer is less than the amount of HPMCAS present in the colloidal dispersion. The film forming polymer may be present in amounts ranging from about 0.2% to about 30% of the weight of HPMCAS in the colloidal dispersion.

Alternatively, in one embodiment, the colloidal dispersion and capsules comprising HPMCAS are substantially free from any other film-forming polymer.

In one embodiment, HPMCAS is the only polymer having enteric properties in the colloidal dispersion or capsule. Thus, in one embodiment the colloidal dispersion and capsules comprising HPMCAS are substantially free from any other polymer having enteric properties, e.g., polymers such as polymethacrylates (copolymer of methacrylic acid and either methyl methacrylate or ethyl acrylate—e.g. Eudragit® enteric family members such as Eudragit® L); CAP (cellulose acetate phthalate); CAT (cellulose acetate trimellitate); HPMCP (hydroxypropyl methylcellulose phthalate); CMEC (Carboxy Methyl Ethyl Cellulose); or polyvinyl derivatives e.g. polyvinyl acetate phthalate (Coateric® family members).

In one embodiment, the colloidal dispersion comprises an optional coloring agent. The coloring agent may be present in an amount ranging from about 0 to about 5% by weight, e.g., from about 0 to about 2.5% by weight, and from about 0 to about 2.0% by weight over the total weight of the colloidal dispersion composition.

In one embodiment, the aqueous compositions described herein further comprise at least one film forming aid.

In one embodiment, film forming aids are selected from rheology modifiers, structuring agents, surfactants, plasticizers, and mineral charges e.g., hypromellose; alkyl cellulose (e.g. carboxy methylcellulose CMC) and other cellulosic derivatives (e.g. HPC, EC, MC, CMEC, HPMCP); polyvinyl acetate derivatives (PVAP); polysaccharides; glyceryl esters; glycol esters; sorbitan monoesters; sorbitan polyoxyethylene esters; polyoxyethylene (POE) ethers; glycerol; polyethylene glycols; polyols; fatty acid esters; glycerol polyethylene, glycol ricinoleate; macrogolglycerides; sodium lauryl sulfate (SLS); triethyl citrate (TEC); acetyl trialkyl citrate; glycerol triacetate (triacetine); alkyl phthalate; talc; silica (Syloid 244FP from Grace) and mixtures thereof. See WO 2013/164121.

In one embodiment, film forming aids that display both plasticizing and viscosity enhancing properties are selected from: glyceryl esters (e.g. glyceryl monooleate and monolinoleate, medium chain triglycerides—i.e. $C_6$-$C_{12}$ fatty acid esters of glycerol); glycol esters (e.g. propylene glycol dicaprylocaprate and monolaurate); sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; polyethylene glycols (e.g. PEG 4000, PEG 6000); glycerol polyethylene, glycol ricinoleate; linoleoyl macrogolglycerides; sucrose esters; silica and mixtures thereof.

In one embodiment, film forming aids are selected from: sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; polyvinyl acetate derivatives (PVAP), cellulosic derivatives (e.g. HPMC, HPC, EC, MC, CMEC, HPMCAS, HPMCP, CAP, CA, CMCAB), polyacrylic acid esters, silica and mixtures thereof.

In one embodiment, film forming aids are present in the aqueous composition in an amount ranging from about 0% to about 20% by weight, such as about 0% to about 15% by weight, or about 0% to about 10% by weight, over the total weight of the aqueous composition of the present disclosure. In other embodiments, film forming aids are present in the aqueous composition in an amount ranging from about 0.05% to about 10% by weight, from about 1% to about 10% by weight, over the total weight of the aqueous composition of the present disclosure.

In one embodiment, the aqueous compositions described herein do not include a gelling agent that undergoes cold gelation, that is, gelation that occurs on transition of the polymer solution and additives from a temperature above the gelling temperature of the particular polymer to a temperature below the gelling temperature. Typical gelling temperatures for cold gelling components are found in the range of 35° C. to 5° C. Examples of gelling agents that undergo cold gelation include polysaccharides and gums, such as carrageenan, gellan gum, guar gum, xanthan gum, andraganth gum, agar agar, pectin, curdlan, gelatin, furcellaran, tamarind seed, or locust bean gum.

In one embodiment, the aqueous compositions described herein do not include a thermogelling agent. A thermogelling agent is an added component that undergoes gelation on transition of the polymer solution and additives from a temperate below the gel temperature to a temperature above the gelling temperature. Typical gelling temperatures for thermogelling components are found in the range of 30° C. to 60° C. Examples of thermogelling agents include polyoxyethylene-polyoxypropylene-polyoxyethylene tri-block copolymers, cellulose derivatives, polysaccharides, and mixtures thereof. Thus, in some embodiments, the aqueous colloidal dispersion does not include a polyoxyethylene-polyoxypropylene-polyoxyethylene tri-block copolymer, a cellulose derivative, or a polysaccharide. In such embodiments, the aqueous composition comprises a dispersant selected from anionic alkyl sulfates (e.g., sodium dodecyl sulfate), polysorbates (e.g., polysorbate 20, polysorbate 65, polysorbate 80), and polyvinylalcohol.

In one embodiment, the aqueous compositions described herein do not include a thermogelling agent or a gelling agent that undergoes a cold gelation.

In one embodiment, the colloidal dispersion composition consists essentially of, or consists of, an aqueous colloidal dispersion of HPMCAS; a base; a dispersant, a plasticizer, a non-polymeric ionizable surface modifier selected from the group consisting of organic acids, salts of multivalent cations, and alkaline earth hydroxides, and optionally, (i) an anti-foaming agent, (ii) a coloring agent, (iii) a film-forming aid selected from the group consisting of glyceryl esters, glycol esters, sorbitan monoesters, sorbitan polyoxyethylene esters, polyoxyethylene ethers, glycerol, polyethylene glycols, polyols; fatty acid esters; glycerol polyethylene, glycol ricinoleate, macrogolglycerides, sodium lauryl sulfate, triethyl citrate, acetyl trialkyl citrate, glycerol triacetate, alkyl phthalate, talc; silica, and mixtures thereof, or (iv) a combination thereof. As used herein "consisting essentially of" means that the composition does not include any other base, does not include a multivalent cation alkoxide, does not include a gelling agent that undergoes cold gelation and/or a thermogellation agent, does not include any other film-forming aid, and does not include any additional component that negatively affects the mechanical and/or chemical properties of a film or capsule gel prepared from the composition, e.g., the disintegration profile, dissolution profile, film thickness, or combinations thereof. For example, the composition does not include an alkoxide other than a sodium or potassium alkoxide, a poloxamer, a gum, a cellulose derivative other than HPMCAS, or a polysaccharide. In some examples, the non-polymeric, ionizable surface modifier is an alkaline earth hydroxide (e.g., $Ca(OH)_2$, $Mg(OH)_2$), and the hydroxide also serves as the base. In some examples, the base is selected from the group consisting of KOH, NaOH, $NH_4OH$, $Ca(OH)_2$, $Mg(OH)_2$, sodium alkoxides, potassium alkoxides, triethyl amine, quinuclidine, morpholine, ethylene diamine, diethylene triamine, N-methyl morpholine, arginine, and lysine, and the non-polymeric, ionizable surface modifier is an organic acid or a salt of a multivalent cation.

In one embodiment, the colloidal dispersion composition consists essentially of, or consists of, an aqueous colloidal dispersion of HPMCAS; a base; a dispersant, a plasticizer, and a non-polymeric ionizable surface modifier selected from the group consisting of organic acids, salts of multivalent cations, and alkaline earth hydroxides. In some examples, the non-polymeric, ionizable surface modifier is an alkaline earth hydroxide (e.g., $Ca(OH)_2$, $Mg(OH)_2$), and the hydroxide also serves as the base. In some examples, the base is selected from the group consisting of KOH, NaOH, $NH_4OH$, $Ca(OH)_2$, $Mg(OH)_2$, sodium alkoxides, potassium alkoxides, triethyl amine, quinuclidine, morpholine, ethylene diamine, diethylene triamine, N-methyl morpholine, arginine, and lysine, and the non-polymeric, ionizable surface modifier is an organic acid or a salt of a multivalent cation.

In one embodiment, the colloidal dispersion composition consists essentially of, or consists of, an aqueous colloidal dispersion of HPMCAS; a base selected from the group consisting of KOH, NaOH, $NH_4OH$, sodium alkoxides, potassium alkoxides, triethyl amine, quinuclidine, morpholine, ethylene diamine, diethylene triamine, N-methyl morpholine, arginine, and lysine; a dispersant, a plasticizer, a non-polymeric ionizable surface modifier selected from the group consisting of organic acids and salts of multivalent cations, and optionally, (i) an anti-foaming agent, (ii) a coloring agent, (iii) a film-forming aid selected from the group consisting of glyceryl esters, glycol esters, sorbitan monoesters, sorbitan polyoxyethylene esters, polyoxyethylene ethers, glycerol, polyethylene glycols, polyols; fatty acid esters; glycerol polyethylene, glycol ricinoleate, macrogolglycerides, sodium lauryl sulfate, triethyl citrate, acetyl trialkyl citrate, glycerol triacetate, alkyl phthalate, talc; silica, and mixtures thereof, or (iv) a combination thereof. As used herein "consisting essentially of" means that the composition does not include any other base, does not include a multivalent cation alkoxide, does not include a gelling agent that undergoes cold gelation and/or a thermogellation agent, does not include any other film-forming aid, and does not include any additional component that negatively affects the mechanical and/or chemical properties of a film or capsule gel prepared from the composition, e.g., the disintegration profile, dissolution profile, film thickness, or combinations thereof. For example, the composition does not include a hydroxide-containing compound other than KOH, NaOH, and $NH_4OH$, an alkoxide other than a sodium or potassium alkoxide, a poloxamer, a gum, a cellulose derivative other than HPMCAS, or a polysaccharide.

In one embodiment, the colloidal dispersion composition consists essentially of, or consists of, an aqueous colloidal dispersion of HPMCAS; a base selected from the group consisting of KOH, NaOH, $NH_4OH$, sodium alkoxides, potassium alkoxides, triethyl amine, quinuclidine, morpholine, ethylene diamine, diethylene triamine, N-methyl morpholine, arginine, and lysine; a dispersant, a plasticizer, and a non-polymeric ionizable surface modifier selected from the group consisting of organic acids and salts of multivalent cations.

Colloidal Dispersion Properties

The colloidal dispersion has properties conducive to manufacture of capsules using conventional manufacturing processes. The colloidal dispersion is capable of thermogelling even in the absence of a conventional thermogelling polymer. By "thermogelling" it is simply meant that the colloidal dispersion exhibits a sharp increase in viscosity at a temperature in the range of about 20-70° C. This increase in viscosity is not necessarily due to conventional thermogelling phenomena as observed for solutions of polymers such as methylcellulose, i.e. HPMC. Rather, it may be due to aggregation of the colloidal HPMCAS particles or other physical processes that result in increased viscosity. The viscosity of the fluid can be measured by shearing between a narrow gap, such as between two plates, one rotating, separated by a narrow gap (e.g., 250 microns) as is the case in a standard shear rheometer. The increase in viscosity may be associated with aggregation of individual (pseudo)latex particles into larger aggregates. Pseudolatexes are colloidal dispersions of spherical solid or semisolid particles, less than 1 micron in diameter, formed from a water-insoluble polymer. If the weight % of solids in the colloidal dispersion is sufficient the aggregation will continue until the some or most of the solids have aggregated into a continuous packed structure. The aggregated colloidal dispersion can adhere to surfaces. Such aggregated colloidal dispersions are capable of forming films upon continued heating, and are suitable for use in manufacture of capsules using conventional dip molding techniques.

In one embodiment the minimum film-forming temperature (MFFT) of the aqueous compositions described herein, when measured with a conventional MFFT-bar from Rhopoint, ranges from about 10° C. to 60° C., e.g., from about 20° C. to 50° C. or about 20° C. to 40° C. The MFFT described is the lowest temperature at which the particles in polymer dispersion can become a continuous, clear and mechanically stable film on drying. Drying a film of the dispersion such that the film remains at temperatures below the minimum film forming temperature leaves a mechanically unstable and brittle film. The MFFT is a parameter of aqueous compositions to be used in the manufacture of hard capsules that is well known to any skilled person.

In one embodiment, the majority of the HPMCAS polymer in the colloidal dispersion is present as small, colloidal particles. "Colloidal particles" means a plurality of small particles in which the average size of the particles in dispersion is less than about 1 micron. By "average size" is meant the effective cumulant diameter, which may be measured by any conventional technique, such as dynamic light scattering using a particle sizing instrument. Preferably, of the fraction of HPMCAS is present as submicron particles, the average size of the submicron particles is in the range of from 0.05 to 5 microns, or more preferably, may range from 0.1 to 1 microns, or more preferably, may range from 0.15 to 0.5 microns.

In one embodiment, a fraction of the HPMCAS may be present as larger aggregates of submicron particles. By 'aggregates' is meant that multiple submicron particles have come together to act as one larger particle composed of multiple smaller particles. The average size of particle aggregates is measured by conventional techniques such as optical light microscopy or using a particle sizing instrument. Preferably, of the fraction of HPMCAS present in particles larger than 1 micron, the average size of the multiparticle aggregates is less than about 100 microns, less than about 50 microns, less than about 20 microns, less than about 10 microns, or less than about 5 microns. In certain embodiments, the average size of the submicron particles ranges from 1 to 100 microns, or may range from 1 to 20 microns, or may range from 1 to 5 microns.

The pH of the colloidal dispersion ranges from 3.6 to 5.3. Preferably, the pH ranges from 4.0 to 4.5 for colloidal dispersions containing organic acids as a non-polymeric ionizable surface modifier, or more preferably 4.0 to 4.4, or more preferably 4.0 to 4.3, or more preferably 4.0 to 4.2, or more preferably 4.0 to 4.1. Preferably, the pH ranges from 4.8 to 5.1 for colloidal dispersions containing compounds of multivalent cations as a non-polymeric ionizable surface modifier, or more preferably 4.9 to 5.1, or more preferably 5.0 to 5.1.

In one embodiment, the viscosity of the aqueous compositions described herein, when measured at 21° C. with a standard shear rheometer equipped with a 40 mm parallel plate geometry running at a shear rate of 40 $s^{-1}$ with a gap of 250 microns, ranges from about 10 cP to about 250 cP. More preferably the viscosity of the pseudolatex ranges from about 50 cP to about 150 cP.

In one embodiment, the glass transition temperature of dried films prepared from the colloidal dispersion, when measured by standard thermochemical techniques such as differential scanning calorimetry or dynamic mechanical analysis, ranges from 15 to 120 degrees Celsius. By glass transition temperature is meant the temperature at which the film transitions from a glassy solid state to a softer rubbery state due to a mobility change in the polymer chains comprising the film. This transition is normally accompanied by an increase in the heat capacity of the film and can be quantified by measuring heat required to warm a film. In certain embodiments the glass transition temperature ranges from about 30° C. to about 120° C., or, more preferably from about 40 to about 80° C.

Zeta potential is a measurement of electrokinetic potential in colloidal dispersions, and is an indicator of the stability of the colloidal dispersion. The magnitude of the zeta potential corresponds to the degree of electrostatic repulsion between similarly charged particles in the dispersion. A greater zeta potential magnitude (positive or negative) indicates a more stable dispersion. In one embodiment, the zeta potential of the colloidal dispersion ranges from zero to minus 60 millivolts, as measured by a standard Phase Analysis by Light Scattering device. A standard zeta potential measurement uses the Brookhaven ZetaPALS instrument operated at a frequency of 2 Hz and an operating voltage of 6.0V using a AQ336 electrode immersed in a 0.10-0.20 wt % HPMCAS pseudolatex dispersion (diluted from the parent concentrated pseudolatex using distilled water). More preferably the zeta potential of the colloidal dispersion ranges from minus 10 to minus 50 millivolts, or more preferably from minus 10 to minus 40 millivolts, or more preferably, from minus 10 to minus 30 millivolts, or more preferably from minus 10 to minus 20 millivolts.

Process for Making Colloidal Dispersion

The colloidal dispersion compositions are prepared by first forming small particles of HPMCAS, stabilizing the particles with an appropriate dispersant, and then concentrating the dispersions while maintaining an appropriate pH or concentration of non-polymeric ionizable surface modifier.

Sub-micron HPMCAS particles may be made by various methods. Particular process embodiments include emulsion, precipitation (for example by pH control or by solvent/non-solvent interaction), and wet milling.

In one embodiment, the colloidal dispersion is prepared using an emulsion process. An organic phase is prepared by adding HPMCAS to an organic solvent. Exemplary organic solvents include ethyl acetate, methyl ethyl ketone, acetone, butanol, isopropyl alcohol, THF, methylene chloride, and miscible mixtures thereof. The HPMCAS is stirred until dissolved, or otherwise uniformly dispersed in the organic phase. The plasticizer or non-ionic dispersant may also be added to the organic phase.

Preferably, the concentration of HPMCAS present in the organic phase ranges from 5 to 23 wt %, or from 8 to 20 wt % or from 11 to 17 wt %.

The amount of plasticizer added to the organic phase ranges from 0% to 40% of the amount of HPMCAS present in the organic phase.

In an independent embodiment a non-ionic surfactant is added only to the organic phase.

The amount of non-ionic dispersant added to the organic phase ranges from 0.1 to 40%, or more preferably, 1.0% to 20% of the amount of HPMCAS present in the organic phase.

An aqueous phase is also prepared. A sufficient amount of anionic or non-ionic dispersant is added to the aqueous phase and dissolved. The amount of anionic dispersant present in the aqueous phase ranges from 0.1% to 10.0% of the amount of HPMCAS present in the organic phase, or more preferably, 1.0% to 3.5% of the amount of HPMCAS present in the organic phase. The amount of non-ionic dispersant added to the aqueous phase ranges from 0.1 to 40%, or more preferably, 1.0% to 20% of the amount of HPMCAS present in the organic phase.

In an independent embodiment, a non-ionic surfactant is added solely to the aqueous phase.

In an independent embodiment, a non-ionic surfactant is added to both the aqueous and organic phases.

In addition, a sufficient amount of base is added to the aqueous phase so that when combined with the organic phase, the HPMCAS will be partially neutralized. As used herein, "base" refers to at least one basic compound or basic composition capable of neutralizing succinic acid groups on HPMCAS, including but not limited to basic hydroxide compounds such as potassium hydroxide (KOH), sodium hydroxide (NaOH), calcium hydroxide ($Ca(OH)_2$), or other basic compounds or compositions, for example, ammonium hydroxide. Other suitable bases include organic alkoxides including methoxides, ethoxides, propoxides, butoxides of sodium, potassium, calcium or magnesium. Other suitable bases include high $pK_a$ organic amines in both monomeric and polymeric form: triethyl amine, quinuclidine, morpholine, ethylene diamine, diethylene triamine, N-methyl morpholine, arginine, and lysine. Known molar equivalence points for the acidity of HPMCAS polymer grades are used to calculate the amount of basic compound to add to aqueous phase preparations. The amount of the basic compound present in aqueous phase ranges from 0 to about 0.4 millimoles of basic compound per gram HPMCAS-H present in the organic phase, or from 0 to about 0.60 millimoles of basic compound per gram HPMCAS-M present in the organic phase, or from 0 to about 0.8 millimoles of basic compound per gram HPMCAS-L present in the organic phase.

In an independent embodiment, the organic phase and aqueous phase are combined to form an emulsion. The mixture is rapidly mixed, such as by stirring, high shear mixing or homogenization. The resultant emulsion obtained by mixing consists of finely divided organic emulsion droplets of submicron average droplet size in a continuous aqueous phase.

Following formation of the emulsion, substantially all of the organic solvent is removed. By "substantially all" it is meant that at least 90% of the solvent is removed. This results in a dispersion of solid particles in an aqueous phase composed of HPMCAS, dispersant, and plasticizer.

The non-polymeric, ionizable surface modifier is then added to the emulsion. When the non-polymeric, ionizable surface modifier is an organic acid, the organic acid may be added to the emulsion to adjust the pH to a range of from about 4 to about 4.5. The emulsion may then be concentrated by removal of water. For example, water may be removed using vacuum, filtration or any other conventional process. The pH of the concentrated emulsion may then be adjusted again to a range of from about 4 to about 4.5 using the corresponding organic acid. This may be followed by another step of removing water. In one embodiment, at least a portion of the water that is removed is returned following addition of the non-polymeric, ionizable surface modifier.

When the non-polymeric, ionizable surface modifier is a material composed of a multivalent cation and one or more anions, following removal of the organic solvent, water may be removed from the emulsion to concentrate the dispersion to the desired solids content. The compound of the multivalent cation may then be added to the dispersion. In one embodiment, the compound of the multivalent cation may be added by the slow addition of a solution of a compound of the multivalent cation. In one preferred embodiment, the concentration of the multivalent cation in the solution being added is less than 100 millimoles per liter, preferably less than 50 millimoles per liter. Exemplary compounds include calcium chloride, calcium acetate, magnesium sulphate, magnesium chloride, and magnesium acetate.

In an independent embodiment, the non-polymeric, ionizable surface modifier is added to the emulsion prior to or during removal of the organic phase. In one embodiment, the non-polymeric, ionizable surface modifier is added to prior to removal of about 20 wt % of the organic phase by rotary evaporation. In another embodiment, the non-polymeric, ionizable surface modifier is added to prior to removal of about 50 wt % of the organic phase by rotary evaporation. In another embodiment, the non-polymeric, ionizable surface modifier is added to prior to removal of about 70 wt % of the organic phase by rotary evaporation. In another embodiment, the non-polymeric, ionizable surface modifier is added to prior to removal of about 80 wt % of the organic phase by rotary evaporation.

In an independent embodiment, the non-polymeric, ionizable surface modifier is added to a dilute solution prior to concentration of the aqueous colloidal dispersion. In one embodiment, the non-polymeric, ionizable surface modifier is added to a dilute solution such that upon completion of addition, the solids concentration is less than about 20 wt %. In other embodiments, the solids concentration following addition of the non-polymeric, ionizable surface modifier may be less than about 15 wt %, or may be less than about 10 wt %, or may be less than about 5 wt %, or may be less than about 2.5 wt %, or preferably may be less than about 1 wt %.

In an independent embodiment, the non-polymeric, ionizable surface modifier is added to the organic phase prior to or during emulsion formation. For example, the surface modifier may be added to the organic phase when the surface modifier is an organic acid with poor water solubility (i.e. a solubility low enough that not all of the desired amount of non-polymeric ionizable surface modifier will be soluble in the aqueous phase volume). The organic phase (containing HPMCAS, plasticizer and non-polymeric ionizable surface modifier) and aqueous phase (containing base and surfactant) are then combined to form an emulsion as described above. Following formation of the emulsion, substantially all of the organic solvent is removed. This process results in a dispersion of solid particles in an aqueous phase composed of HPMCAS, dispersant, plasticizer and non-polymeric ionizable surface modifier.

Aqueous colloidal dispersions prepared by embodiments of the disclosed method are structurally different and as a result and have different properties than comparable colloidal dispersions formed by combining the HPMCAS polymer (e.g. fine grade HPMCAS-LF, -MF or -HF available from Shin-Etsu), a base (e.g., $Ca(OH)_2$), a dispersant, and a plasticizer in water to form an aqueous dispersion. For example, aqueous colloidal dispersions prepared by the disclosed method are visually homogeneous (i.e., no visible particles to the naked eye), and have a smaller average particle size (as measured by DLS) (see, e.g., Example 13 infra). In some examples, the aqueous colloidal dispersion comprises particles having an average size, as measured by DLS, less than 1 μm, such as less than 750 nm, preferably less than 500 nm with no particles larger than 5 μm visible by microscopy at 50× magnification. In contrast, comparable compositions formed by combining all of the components in water include visible particles, such as particles having an average size greater than 1 μm as measured by DLS with particles greater than 20 μm visible by microscopy at 50× magnification. The differences in these properties facilitate thermogelling in contrast to comparable compositions formed by another method, which do not exhibit thermal gelling (see, e.g., FIGS. 3 and 4). Wet mounted films formed by embodiments of the disclosed method also appear smoother and more homogeneous when viewed with a microscope than films formed from a comparable composition made by another method (see, e.g., FIGS. 1 and 2).

Capsules

In another aspect, the colloidal dispersion has appropriate solids content, gelling and setting properties, and rheological behavior for use in the manufacture of capsule shells. Capsules may be prepared from the colloidal dispersion composition using any conventional process. For example, a dip-molding processes for the manufacture of hard capsules may be used. The process comprises providing a bath of the colloidal dispersion at a temperature below the gelling temperature. Molding pins pre-heated to a temperature above the gelling temperature are dipped into the colloidal dispersion. The molding pins are withdrawn, forming a film on the molding pins. The film formed on the molding pins surface can then be dried, stripped off the pins and cut to a desired length, thereby obtaining the capsule caps and bodies.

Capsule Properties and Dosage Forms

In one embodiment, the capsules made from the colloidal dispersion have bulk enteric properties.

In one embodiment, the capsules manufactured from the colloidal dispersion are resistant to disintegration in demineralized water for at least 10 minutes, such as for example at least 15, 20, 25, or 30 minutes.

Dosage forms may be prepared using capsules made from the colloidal dispersion. Such dosage forms comprise at least one active ingredient. The active ingredient may be liquid or solid, and the capsule may be filled using any conventional technique. The capsules may be sealed or banded according to conventional techniques. Alternatively, the capsules may be manufactured to have a specific mechanical design, e.g., the ability to pre-lock empty caps and bodies, or completing the filling steps in a different location, or at a specific time. Examples of such designs may be found in, for example, WO 2009/138920 and WO 2009/050646.

In one embodiment, a dosage form comprising capsules formed from the colloidal dispersion releases less than about 10 wt % of the total encapsulated active ingredient during the initial two hours following administration to an in vitro simulated gastric dissolution media having a pH of about 1.2.

In another embodiment, a dosage form comprising capsules made from the colloidal dispersion releases at least about 80% of the total encapsulated active ingredient during the initial 45 minutes after administration to an in vitro simulated intestinal dissolution media having a pH of about 6.8.

The invention will now be illustrated with particular reference to the following non-limiting examples. Numerous other embodiments are possible, which are consistent with the present disclosure.

EXAMPLES

Preparation of HPMCAS Colloidal Dispersions

| Table of Examples 1 to 3 (Multivalent cations) | | | |
|---|---|---|---|
| Example # | 1 | 2 | 3 |
| Base Material used for prep | — | — | — |
| HPMCAS M-grade | 12.8 g | 12.8 g | 76.41 g |
| ATEC | 3.6 g (23.10%)* | 2.82 g (22.00%) | 16.47 g (21.55%) |
| SLS | 0.38 g (2.80%) | 0.384 g (3.00%) | 2.82 g (3.69%) |
| NaOH | 0.102 g (0.79%) | — | 0.608 g (0.795%) |
| Acetic Acid | None | None | None |
| Cation Compound | $CaCl_2$ | $Ca(OH)_2$ | $CaCl_2$ |
|  | 0.414 g (3.23%) | 0.095 g (0.742%) | 2.539 g (3.32%) |
| Wt % Solids | 21.3 | 25.0 | 24.8 |
| Final pH | 5.0 | 5.01 | 4.9 |
| Thermogellation | Yes | Yes | Yes |

*values in parentheses are % relative to HPMCAS

Example 1

In a 125 ml Erlenmeyer flask containing 80 ml of ethyl acetate, 12.8 grams of HPMCAS (medium granular (MG) grade available from Shin-Etsu) was rapidly dispersed and stirred until dissolved. Acetyl triethylcitrate (3.6 grams) was added to the HPMCAS/ethyl acetate solution with stirring continued until the acetyl triethylcitrate was completely dispersed. In a separate flask, an aqueous solution of 0.38 grams sodium lauryl sulfate, and 0.102 grams of sodium hydroxide in 330 mL water was prepared. A pre-emulsion was prepared by slowly adding the organic solution to the aqueous solution while a rapidly stirring followed by high shear mixing at 10,000 rpm for 5 minutes with a Polytron PT3100 mixer. The pre-emulsion was then transferred to a homogenizer (Microfluidics 110s) and cycled for 12 minutes resulting in an emulsion with uniform consistency. The resulting emulsion was then transferred to a 2 liter round-bottom flask and placed on a roto-evaporator maintained at 30° C. under vacuum at 80 to 120 millibar with rotation at 150 rpm until substantially all the ethyl acetate was removed. By "substantially all" is meant that no further ethyl acetate could be removed from the emulsion by rotary evaporation under the present conditions, i.e., at least 90% of the ethyl acetate was removed. The flask containing the dispersion was removed from the roto-evaporator. The emulsion was stirred with a magnetic stir bar while a solution of 0.414 grams of calcium chloride in 145 mL distilled water was slowly added. A single drop of Silfar silicone anti-foaming agent was added to the emulsion. The mixture was then roto-evaporated under vacuum at 30° C. at 5-20 millibar at a rotational speed of 150 rpm to remove the remaining water until a final mass of 53 grams, 21.3 wt % solids, was obtained. The measured pH was 4.9. Thermogelling behavior was demonstrated on a standard shear rheometer using a thermal scanning program by heating the sample from 5 to 80° C. in oscillatory shear mode using 1% oscillatory strain at 1 Hz frequency. Thermogelation was observed as a sharp increase in the complex viscosity of the sample by about three orders of magnitude at a temperature of about 38° C.

Example 2

An HPMCAS colloidal dispersion was prepared according to Example 1 with the following modifications. Sodium hydroxide was omitted in the aqueous phase of the emulsion. The coarse emulsion was formed as in Example 1, and solid calcium hydroxide (0.095 g) was added while being mixed on the Polytron PT3100 mixer. The final concentrated colloidal dispersion was then prepared according to Example 1 by removal of the remaining water by rotary evaporation.

Example 3

An HPMCAS colloidal dispersion was prepared according to Example 1 with 16.47 g ATEC and scaling up the preparation by a factor of 6. Calcium chloride (2.539 g) was added in a single aliquot in 250 mL water to the coarse emulsion formed after high shear mixing. The flask was transferred to a rotary evaporator and substantially all the ethyl acetate was removed. The flask containing the dispersion was removed and a dropwise addition of calcium chloride solution (2.539 g total $CaCl_2$) was performed as in Example 1 to the concentrated colloidal dispersion. The final concentrated colloidal dispersion was then prepared according to Example 1 by removal of remaining water by rotary evaporation.

| Table of Comparative Examples | | | |
|---|---|---|---|
| Example # | C1 | C2 | C3 |
| Base Material used for prep | — | — | — |
| HPMCAS M-grade | 32.0 g | 3.2 g | 64 g |
| ATEC | 6.4 g (20.00%)* | 0.64 g (20.00%) | 18 g (28.12%) |
| SLS | 0.96 g (3.00%) | 0.096 g (3.00%) | 1.92 g (3.00%) |
| NaOH | 0.256 g (0.80%) | 0.0256 g (0.80%) | 0.508 g (0.79%) |
| Acetic Acid | No | No | No |
| Cation Compound | No | No | No |
| Wt % Solids | 28.1 | 17.4 | 28.0 |
| Final pH | 5.1 | 4.8 | — |
| Thermogellation | No | No | No |

| Example # | C4 | C5 |
|---|---|---|
| Base Material used for prep | — | — |
| HPMCAS M-grade | 32.0 g | 153.62 g |
| ATEC | 9.0 g (28.1%) | 33.75 g (21.9%) |
| SLS | 0.96 g (3.00%) | 4.16 g (3.00%) |
| NaOH | 0.256 g (0.80%) | — |
| Acetic Acid | No | No |
| Cation Compound | No | Ca(OH)$_2$ |
| Wt % Solids | 23.3 | 29.5 |
| Final pH | 5.00 | 5.11 |
| Thermogellation | No | No |

*values in parentheses are % relative to HPMCAS

Comparative Example 1

In a 5000 ml Erlenmeyer flask containing 200 ml of ethyl acetate, 32.0 grams of HPMCAS (MG grade from Shin-Etsu) was rapidly dispersed and stirred until dissolved. Acetyl triethylcitrate (6.4 grams) was added to the HPMCAS/ethyl acetate solution with stirring continued until completely dispersed. In a separate flask, an aqueous solution of 0.96 grams sodium lauryl sulfate, and 0.256 grams of sodium hydroxide in 800 mL water was prepared. A pre-emulsion was prepared by slowly adding the organic solution to the aqueous solution while a rapidly stirring followed by high shear mixing at 10,000 rpm for 10 minutes with a Polytron PT3100 mixer. The pre-emulsion was then transferred to a homogenizer (Microfluidics 110s) and cycled for 90 minutes resulting in an emulsion with uniform consistency. The resulting emulsion was then transferred to a 2 liter round-bottom flask and placed on a roto-evaporator maintained at 30° C. under vacuum with rotation until all of the ethyl acetate was removed. The flask containing the emulsion was removed from the roto-evaporator and the receiving flask emptied of organic solvent. The mixture was then roto-evaporated to remove water until a final concentration of 30 wt % solids was obtained.

Comparative Example C2

An HPMCAS colloidal dispersion was prepared according to Comparative Example C1, but was scaled down by a factor of 10.

Comparative Example C3

An HPMCAS colloidal dispersion was prepared according to Comparative Example C1, but was scaled up by a factor of 2.

Comparative Example C4

An HPMCAS colloidal dispersion was prepared according to Comparative Example C1, but with the ATEC concentration increased to 28% relative to the amount of HPMCAS in the organic phase.

Comparative Example C5

HPMCAS-MF (153.62 g) and 4.61 g sodium lauryl sulfate were suspended in 460 mL MilliQ water and high shear mixed using a polytron 3100 mixer for 5 minutes. Calcium hydroxide (1.140 g) was then added as an aqueous slurry (20 mL) to the dispersion with while high shear mixing. ATEC (33.75 g) was then added dropwise and the suspension was allowed to mix using an anchor paddle stirrer overnight. The suspension was then filtered through a standard mesh screen (425 μm) to remove large particles.

| Table of Examples 4 to 6 | | | |
|---|---|---|---|
| Example # | 4 | 5 | 6 |
| Base Material used for prep | C1 (IRD202-089) | C2 (IRD202-077B) | C3 (IRD212-090B) |
| HPMCAS M-grade | 32.0 g | 3.2 g | 64 g |
| ATEC | 6.4 g (20.00%)* | 0.64 g (20.00%) | 18 g (28.12%) |

-continued

Table of Examples 4 to 6

| Example # | 4 | 5 | 6 |
|---|---|---|---|
| SLS | 0.96 g (3.00%) | 0.096 g (3.00%) | 1.92 g (3.00%) |
| NaOH | 0.256 g (0.80%) | 0.0256 g (0.80%) | 0.508 (0.79%) |
| Acetic Acid | No | No | — |
| Cation Compound | $MgCl_2$ | $MgCl_2$ | $Mg(acetate)_2$ |
|  | 0.213 g (0.66%) | 0.024 g (0.75%) | 3.09 g (4.82%) |
| Wt % Solids | 28.1 | 17.4 | 28.0 |
| Final pH | 5.1 | 4.8 | — |
| Thermogellation | Yes | Yes | Yes |

*values in parentheses are % relative to HPMCAS

Example 4

An HPMCAS colloidal dispersion was prepared using Comparative Example C1 as a starting material. A 1.0 M magnesium chloride solution was added to the product of Comparative Example 1 to achieve a final magnesium chloride content of 0.213 g. The addition was performed by dropwise addition of the magnesium chloride solution to the concentrated colloidal dispersion with high shear mixing on a Polytron 3100 mixer.

Example 5

An HPMCAS colloidal dispersion was prepared using Comparative Example C2 as a starting material. A 1.0 M magnesium chloride solution was added to the product of Comparative Example C2 to a final magnesium chloride content of 0.024 g. The addition was performed by dropwise addition of the magnesium chloride stock solution to the concentrated colloidal dispersion with high shear mixing on a Polytron 3100 mixer.

Example 6

An HPMCAS colloidal dispersion was prepared using Comparative Example C3 as a starting material. A 1.0 M magnesium acetate solution was added to the product of Comparative Example C3 to a final magnesium acetate content of 3.09 g. The addition was performed by dropwise addition of the magnesium chloride solution to the concentrated colloidal dispersion with high shear mixing on a Polytron 3100 mixer.

Example 7

In a 500 ml Erlenmeyer flask containing 200 ml of ethyl acetate, 32.03 grams of HPMCAS (MG grade) was rapidly dispersed and stirred until dissolved. Acetyl triethylcitrate (9.03 grams) was added to the HPMCAS/ethyl acetate solution with stirring continued until completely dispersed. In a separate flask, an aqueous solution of 0.962 grams sodium lauryl sulfate, and 0.256 grams of sodium hydroxide in 800 mL water was prepared. A pre-emulsion was prepared by slowly adding the organic solution to the aqueous solution while rapidly stirring followed by high shear mixing at 10,000 rpm for 5 minutes with a Polytron PT3100 mixer. The pre-emulsion was then transferred to a homogenizer (Microfluidics 110s) and cycled for 20 minutes resulting in an emulsion with uniform consistency. The resulting emulsion was then transferred to a 2 liter round-bottom flask and placed on a roto-evaporator maintained at 40° C. under vacuum with rotation until substantially all the ethyl acetate was removed. The flask containing the colloidal dispersion was removed from the roto-evaporator. 1.0 M acetic acid was added to the flask dropwise while manually agitating the contents until the measured pH was 4.2. The mixture was then roto-evaporated to remove water until approximately 300 mL of the mixture remained. The flask containing the colloidal dispersion was again removed from the roto-evaporator and the pH measured as 4.5. Acetic acid (1.0 M) was added to the flask dropwise while manually agitating the contents until the measured pH was 4.2. The mixture was then roto-evaporated to remove water until approximately 150 mL of the mixture remained. The solids content was measured as 28.4% solids and the pH was 4.5.

Table of Examples 7 to 10 (organic anion)

| Example # | 7 | 8 | 9 | 10 |
|---|---|---|---|---|
| Base Material | C4 (IRD212-070A) | — | — | — |
| HPMCAS M-grade | 2.03 g | 32.08 g | 12.81 g | 583.2 g |
| ATEC | 9.03 g (28.19%)* | 8.97 g (27.96%) | 2.82 g (22.01%) | 127.9 g (21.93%) |
| SLS | 0.962 g (3.00%) | 0.967 g (3.01%) | 0.391 g (3.05%) | 17.49 g (2.99%) |
| NaOH | 0.256 g (.80%) | 0.256 g (0.80%) | 0.102 g (0.79%) | 4.66 g (0.80%) |
| Acetic Acid | Yes | Yes | Yes | Yes |
| Cation Compound | None | None | None | None |
| Wt % Solids | 28.4 | 29.2 | 30.1 | 29.5 |
| Final pH | 4.5 | 4.56 | 4.2 | 4.4 |
| Thermogellation | Yes | Yes | Yes | Yes |

*values in parentheses are % relative to HPMCAS

Example 8

An HPMCAS colloidal dispersion was prepared according to Example 7 with the modifications shown in the table.

Example 9

An HPMCAS colloidal dispersion was prepared according to Example 7, but was scaled down by a factor of 0.4, adding 2.82 g ATEC.

Example 10

An HPMCAS colloidal dispersion was prepared according to Example 9, but was scaled up by a factor of 45.

Table of Example 11 (non-ionic dispersant)

| Example # | 11 | 12 |
|---|---|---|
| HPMCAS | 12.80 g | 12.80 g |
| ATEC | 2.82 g (22.03%) | 3.59 g (28.04%) |
| Non-ionic Surfactant | PS-80 0.032 g (0.25%) | PS-80 0.821 g (6.4%) |
| SLS | 0.36 g (2.81%) | None |
| NaOH | 0.102 g (0.79%) | 0.010 g (0.08%) |
| Acetic Acid | Yes | Yes |
| Cation Compound | None | None |
| Wt % Solids | 23.7 | 50.1 |
| Final pH | 4.19 | 4.94 |
| Thermo-gellation | Yes | Yes |

* values in parentheses are % relative to HPMCAS

Example 11

In a 125 ml Erlenmeyer flask containing 80 ml of ethyl acetate, 12.8 grams of HPMCAS (LG-grade available from Shin-Etsu) was rapidly dispersed and stirred until dissolved. Acetyl triethylcitrate (2.82 g) and 0.032 g of polysorbate-80 was added to the HPMCAS/ethyl acetate solution with continuous stirring until both components were completely dissolved. In a separate flask, an aqueous solution of 0.36 grams sodium lauryl sulfate in 320 mL water was prepared. Sodium hydroxide (0.102 g) was added to the aqueous phase before mixing to form the emulsion. A pre-emulsion was prepared by slowly adding the organic solution to the aqueous solution while a rapidly stirring followed by high shear mixing at 10,000 rpm for 5 minutes with a Polytron PT3100 mixer. The pre-emulsion was then transferred to a homogenizer (Microfluidics 110s) and cycled for 12 minutes resulting in an emulsion with uniform consistency. The resulting emulsion was then transferred to a 2 liter round-bottom flask and placed on a roto-evaporator maintained at 30° C. under vacuum at about 80 to 120 millibar with rotation at 150 rpm until substantially all the ethyl acetate was removed. The flask was removed from the rotary evaporator and acetic acid was added to the dispersion in two separate aliquots during evaporation of the water from the dispersion as in example 7. After the second addition of acetic acid the dispersion was rotary evaporated to remove the remaining water until a final mass of about 50 grams, 23.7 wt % solids, was obtained. The measured pH was 4.19.

Example 12

An HPMCAS colloidal dispersion was prepared according to example 11 with the modifications noted in the table. In this example the polysorbate-80 was added to the aqueous phase instead of the organic phase prior to mixing to form the emulsion. The high weight percent of solids was achieved by extensive rotary evaporation.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

Example 13

Figure 1:
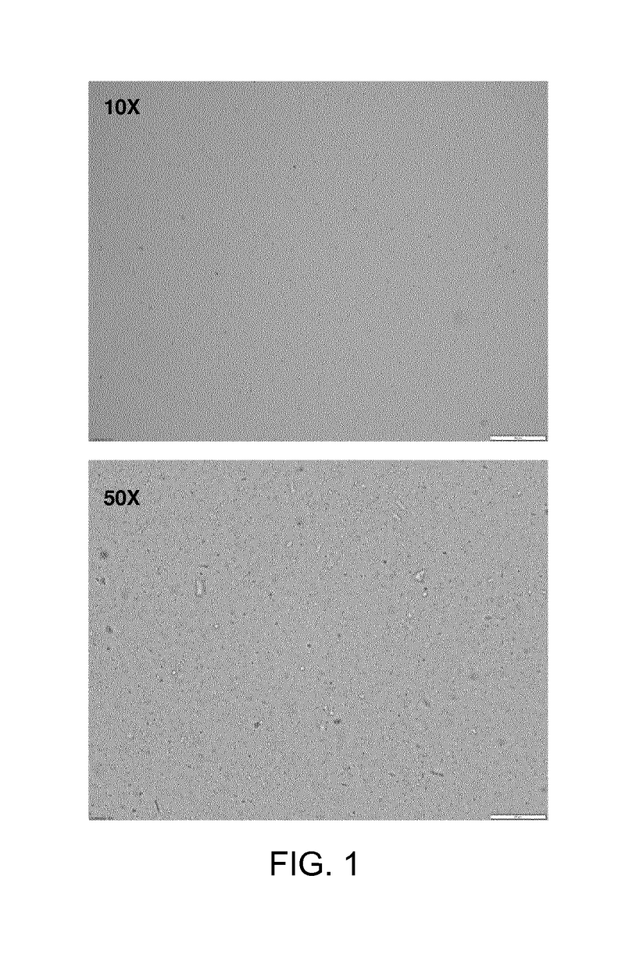
FIG. 1 is two micrograph images showing a film formed from one embodiment of the disclosed aqueous-based compositions using the disclosed emulsion/solvent diffusion method (Example 2). The upper micrograph was obtained at a magnification of 10×; the bottom micrograph was obtained at a magnification of 50×.
Figure 2:
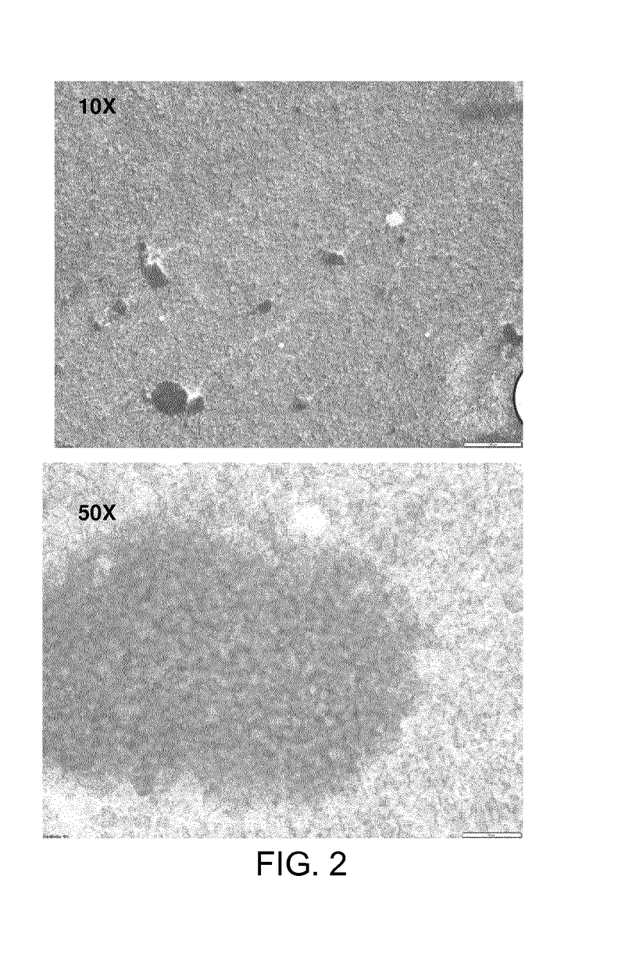
FIG. 2 is two micrograph images showing a film formed using another process (Comparative Example 5). The upper micrograph was obtained at a magnification of 10×; the bottom micrograph was obtained at a magnification of 50×.
Figure 3:
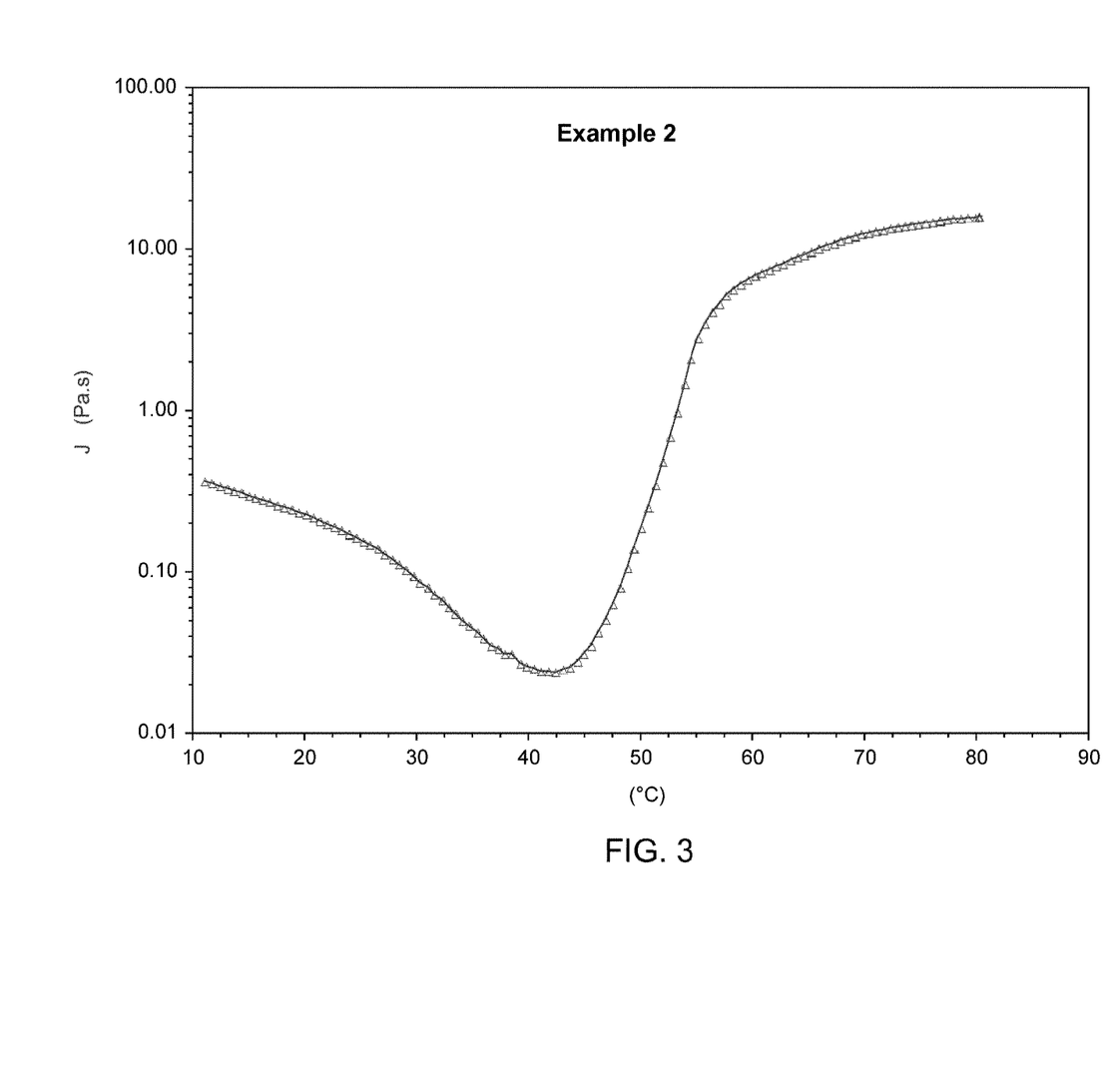
FIG. 3 is a thermal rheology scan of one embodiment of the disclosed aqueous-based compositions (Example 2).
Figure 4:
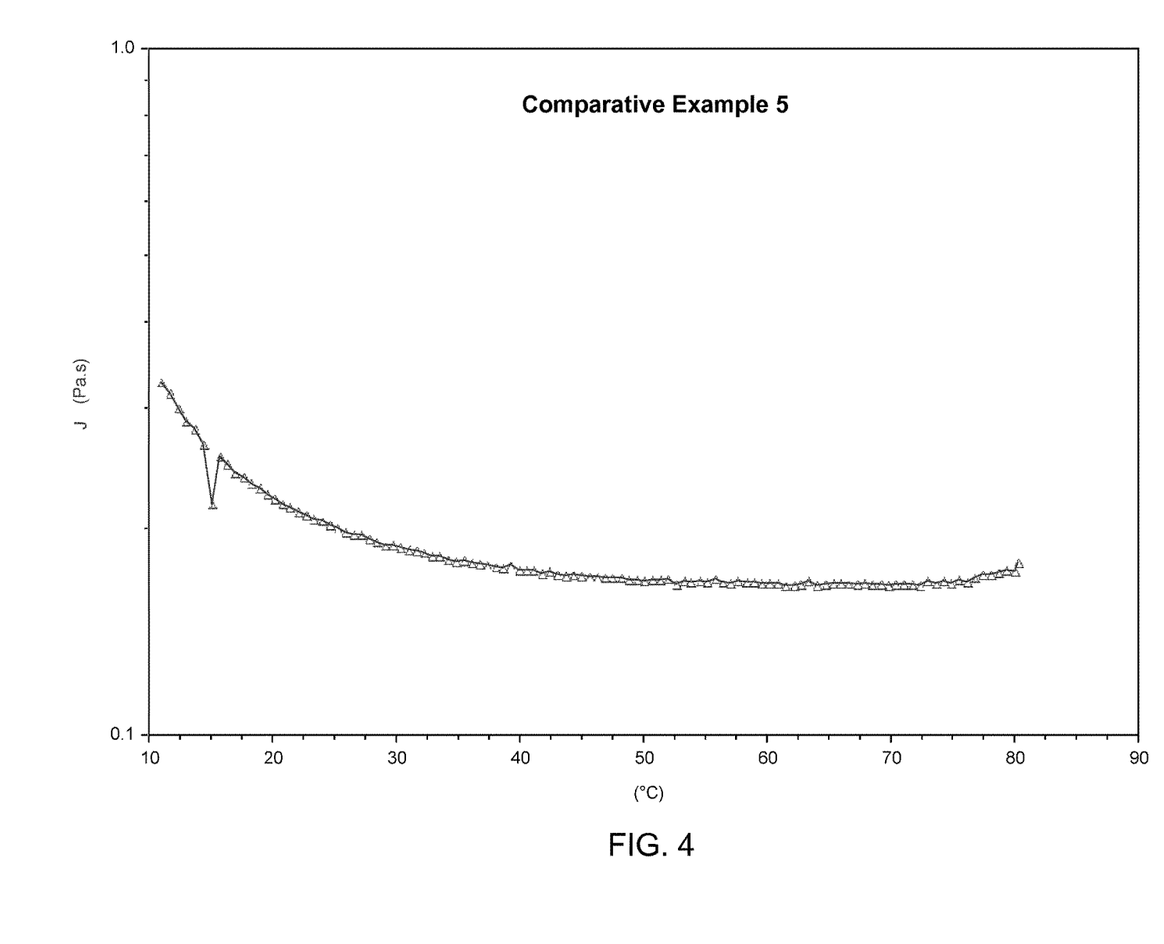
FIG. 4 is a thermal rheology scan of a comparative composition (Comparative Example 5).

The properties of films formed from the compositions of Example 2 and Comparative Example 5 were compared. The findings are summarized in the table below, with the methods following the table. FIGS. 1 and 2 are micrographs demonstrating the difference in homogeneity and particle size of the two preparations. The film from the Example 2 composition visibly is much more homogeneous with markedly smaller particles (FIG. 1) than the film formed from the composition of Comparative Example 5 (FIG. 2). FIGS. 3 and 4 are thermal rheology scans of the films formed from the compositions of Example 2 and Comparative Example 5, respectively. As seen in FIG. 3, the film produced by the composition of Example 2 shows a pronounced dip between 40-45° C. indicating the thermal gelation temperature. In contrast, the film produced by the composition of Comparative Example 5 shows no thermal gelation over the temperature range from 10-90° C.

Table of Example 13 (comparison)

| Parameter | Example 2 | Comparative Example 5 |
|---|---|---|
| Process | Emulsion/solvent diffusion method using HPMCAS-MG | Aqueous dispersion prepared from HPMCAS-MF |
| Visual Homogeneity | visually homogeneous | particles visible to naked eye |
| Solid content | 25.0% | 29.5% |
| pH | 5.08 | 5.11 |
| Average particle size (by DLS) | 337 nm | 1071 nm |
| Viscosity at 40 s$^{-1}$ at 21° C. | 17 cP | 312 cP |
| Thermal rheology of base latex | Thermogelling | Non-thermogelling |
| Microscopic Homogeneity at 50X magnification | No particles >5 μm observable | Particles <20 μm observable |

Methods for Table of Example 13 (Comparison)

Visual homogeneity was assessed by observation of the dispersion by a single experimenter. A positive result was indicated by the presence of particles visible to the naked eye. The absence of particles visible to the naked eye was taken as a negative result.

Solids content was measured by placing an 200-250 mg aliquot of the dispersion into an aluminum weigh pan, previously weighed and recorded, and weighing the pan plus the aliquot of dispersion. The pan with dispersion was then dried at 95° C. on a hot plate for 30 minutes and the pan and dried dispersion were reweighed. The solid content was taken as $$\text{wt \% solids} = \frac{[(\text{pan} + \text{wet dispersion}) - (\text{pan})]}{[(\text{pan} + \text{dry dispersion}) - (\text{pan})]}.$$

pH was measured using a standard pH meter and electrode such as model AR15 available from Fischer Scientific.

Particle size was measured by a Brookhaven ZetaPALS instrument operating at 25° C. using the Contin Algorithm to deconvolute the 90° light scattering autocorrelation function. Autocorrelation data was collected over 400 μs.

Viscosity was measured on a TA instruments DHR-2 rheometer equipped with a 40 mm stainless steel flat plate geometry. Measurements were performed at 40 s$^{-1}$ strain rate at 21° C. Thermogelation was assessed using a temperature scanning oscillatory measurement performed from 10 to 80° C. at an oscillation frequency of 1 Hz and strain of 1%.

Microscopy was performed on a Olympus BX53 microscope using wet mounts of the pseudolatexes on glass slides at magnifications of 10×, 20× and 50×.

What is claimed is:

1. A composition comprising:
    an aqueous colloidal dispersion comprising
        partially neutralized hydroxypropyl methyl cellulose acetate succinate (HPMCAS), wherein a percentage of neutralization of acidic groups on the HPMCAS does not exceed 50%,
        a dispersant,
        a plasticizer, and
        a non-polymeric, ionizable surface modifier in an amount of from 0.05 to 1 wt % of the composition, wherein said non-polymeric, ionizable surface modifier is an aliphatic carboxylic acid, a dicarboxylic acid, a hydroxy carboxylic acid, or a benzoic acid,
    wherein the composition has a pH of from 4.0 to 4.3.

2. The composition of claim 1 wherein said non-polymeric, ionizable surface modifier is formic, acetic, propionic, butyric, pentanoic, hexanoic, oxalic, malonic, succinic, glycolic, lactic, malic, tartaric, citric, or mandelic acid.

3. The composition of claim 1, wherein said HPMCAS is present in an amount of from 15-35 wt % of said composition.

4. The composition of claim 1, wherein a major fraction of said HPMCAS is dispersed in said composition and has an average particle size of less than 1 μm.

5. A composition, comprising:
    an aqueous colloidal dispersion comprising
        aggregated, partially-neutralized hydroxypropyl methyl cellulose acetate succinate (HPMCAS), wherein a percentage of neutralization of acidic groups on the HPMCAS does not exceed 50%,
        a dispersant,
        a plasticizer, and
        a non-polymeric, ionizable surface modifier, wherein the non-polymeric, ionizable surface modifier is an aliphatic carboxylic acid, a dicarboxylic acid, a hydroxy carboxylic acid, or a benzoic acid,
    wherein the composition has a pH of from 4.0 to 4.3.

6. The composition of claim 1, wherein said dispersant is anionic.

7. The composition of claim 1, wherein said dispersant is present in an amount of from 0.2 to 0.9 wt % of said composition, or wherein said dispersant is non-ionic and present in an amount of from 0.1 to 40 wt % of HPMCAS.

8. The composition of claim 1, wherein said plasticizer is a tri-alkyl citrate ester, an acetylated-tri-alkyl citrate ester, a di-alkyl phthalate ester, a mono-glycerol ester, a di-glycerol ester, or a benzoate-ester.

9. The composition of claim 1, having a viscosity when measured at 21° C. with a standard shear rheometer of from about 3 cP to about 4000 cP.

10. The composition of claim 1, having a viscosity when measured at 21° C. with a standard shear rheometer of from about 10 cP to about 250 cP.

11. A hard capsule shell made according to a dip-molding process with a composition according to claim 1.

12. A process for making a composition comprising:
    a. dissolving hydroxypropyl methyl cellulose acetate succinate (HPMCAS) and a plasticizer in an organic solvent to form an organic phase;
    b. combining water, a dispersant, and a base to form an aqueous phase;
    c. combining the organic phase and the aqueous phase to form a mixture comprising partially neutralized HPMCAS, wherein a percentage of neutralization of acidic groups on the HPMCAS does not exceed 50%;
    d. homogenizing said mixture to form an emulsion;
    e. removing substantially all said organic solvent from said mixture;
    f. adding a non-polymeric, ionizable surface modifier to said aqueous dispersion, wherein the non-polymeric, ionizable surface modifier is an aliphatic carboxylic acid, a dicarboxylic acid, a hydroxy carboxylic acid, or a benzoic acid;
    g. reducing a pH of said mixture; and
    h. adjusting the water concentration of said mixture by removing water to obtain an aqueous dispersion of partially neutralized HPMCAS having a pH of from 4.0 to 4.3, wherein the non-polymeric, ionizable surface modifier is present in an amount of from 0.05 to 1 wt % of the composition.

13. A process for making a composition comprising:
    a. dissolving hydroxypropyl methyl cellulose acetate succinate (HPMCAS) and a plasticizer in an organic solvent to form an organic phase;
    b. adding a non-polymeric, ionizable surface modifier to said organic phase, wherein the non-polymeric, ionizable surface modifier is an aliphatic carboxylic acid, a dicarboxylic acid, a hydroxy carboxylic acid, or a benzoic acid;
    c. combining water, a dispersant, and a base to form an aqueous phase;
    d. combining the organic phase and the aqueous phase to form a mixture comprising partially neutralized HPMCAS, wherein a percentage of neutralization of acidic groups on the HPMCAS does not exceed 50%;
    e. homogenizing said mixture to form an emulsion;
    f. removing substantially all said organic solvent from said mixture;
    g. reducing a pH of said mixture; and
    h. adjusting the water concentration of said mixture by removing water to obtain an aqueous dispersion of partially neutralized HPMCAS having a pH of from 4.0 to 4.3, wherein the non-polymeric, ionizable surface modifier is present in an amount of from 0.05 to 1 wt % of the composition.

* * * * *